US006219578B1

(12) United States Patent
Collins et al.

(10) Patent No.: US 6,219,578 B1
(45) Date of Patent: Apr. 17, 2001

(54) GALVANIC VESTIBULAR STIMULATION SYSTEM AND METHOD

(75) Inventors: James J. Collins, Newton Centre, MA (US); J. Timothy Inglis, Vancouver (CA)

(73) Assignees: Trustees of Boston University, Boston, MA (US); Universtiy of British Columbia, Vancouver (CA)

( * ) Notice: Subject to any disclaimer, the term of this patent is extended or adjusted under 35 U.S.C. 154(b) by 0 days.

(21) Appl. No.: 09/392,186

(22) Filed: Sep. 9, 1999

Related U.S. Application Data
(60) Provisional application No. 60/099,651, filed on Sep. 9, 1998.

(51) Int. Cl.$^7$ .................................................... A61N 1/36
(52) U.S. Cl. .......................................................... 607/2
(58) Field of Search ................................. 607/2, 54, 48, 607/49, 45, 75

(56) References Cited

U.S. PATENT DOCUMENTS

| | | |
|---|---|---|
| 4,558,703 | 12/1985 | Mark . |
| 4,667,676 | 5/1987 | Guinta . |
| 5,762,612 | 6/1998 | Campbell . |

FOREIGN PATENT DOCUMENTS

| | | |
|---|---|---|
| 3416873 | 11/1985 | (DE) . |
| 0799597 | 10/1997 | (EP) . |
| WO 88/04909 | 7/1988 | (WO) . |

OTHER PUBLICATIONS

Johansson Rolf, Måns Magnusson, Per A. Fransson, "Galvanic Vestibular Stimulation for Analysis of Postural Adaptation and Stability," *IEEE Transactions on Biomedical Engineering*, vol. 42, No. 3, Mar. 1995, pp. 282–292.

*Primary Examiner*—Scott M. Getzow
(74) *Attorney, Agent, or Firm*—Samuels, Gauthier & Stevens, LLP

(57) ABSTRACT

A system and method of altering the output of a vestibular system including providing a source of time-varying galvanic current, transcutaneously delivering time-varying galvanic current to vestibular afferents associated with the vestibular system in order to modulate firing level of the vestibular afferents, and inducing a coherent time-varying sway response that counteracts postural sway. In an alternative embodiment there is provided a galvanic vestibular stimulation system including a source which transcutaneously delivers time-varying galvanic current to vestibular afferents in order to modulate the firing level of the vestibular afferents, a monitor which monitors postural sway thereby providing indication of necessary galvanic current to be delivered. The system induces a coherent time-varying sway response that counteracts the monitored postural sway.

17 Claims, 10 Drawing Sheets

GALVANIC VESTIBULAR STIMULATION SYSTEM AND METHOD

PRIORITY INFORMATION

This application claims priority from provisional application Ser. No. 60/099,651 filed Sep. 9, 1998.

SPONSORSHIP INFORMATION

This invention was made with government support under contract no. DC03484-01 awarded by the National Institutes of Health. The government has certain rights in the invention.

BACKGROUND OF THE INVENTION

The invention relates to the field of vestibular stimulation, and in particular to a galvanic vestibular stimulation system and method.

Galvanic vestibular stimulation has proven to be a valuable technique for studying the role played by vestibular information in the control of stance and balance. With this technique, small-amplitude galvanic current is delivered transcutaneously to the vestibular afferents that lie directly below the mastoid bones. This serves to modulate the continuous firing level of the peripheral vestibular afferents. Specifically, cathodal (negative) currents increase the firing rate of vestibular afferents, whereas anodal (positive) currents decrease the firing rate of vestibular afferents. Thus, constant bipolar galvanic current produces a tonic vestibular asymmetry. This effect causes a standing subject to lean in different directions depending on the polarity of the current and the direction of the subject's head. In general, a subject will tend to lean toward the anodal stimulus (in the direction of the vestibular apparatus with reduced afferent activity levels) and/or away from the cathodal stimulus (away from the vestibular apparatus with increased afferent activity levels).

A considerable number of studies have examined the body-sway response to constant galvanic stimulation of the vestibular system. One study, for instance, used monopolar monaural constant galvanic stimulation and demonstrated that the amplitude of the body-sway response increases linearly with increasing stimulus current (from 0.2 mA to 1.0 mA). Another study used bipolar binaural constant galvanic stimulation and showed that the direction of the evoked sway is approximately in the direction of the intermastoid line. Thus, with bipolar binaural constant galvanic stimulation, lateral sway is produced if a subject's head is facing forward, whereas anteroposterior sway is produced if a subject's head is turned to the left or right (over the left or right shoulder).

A limited number of studies have shown that the application of sinusoidally varying bipolar galvanic currents to the vestibular system can lead to sinusoidally-varying postural sway. With sinusoidal galvanic stimulation, as with constant galvanic stimulation, the body tends to sway towards the positive stimulus and away from the negative stimulus. For low-frequency stimulation, the frequency of the evoked body sway matches the frequency of the stimulus, whereas the amplitude of the evoked body sway varies from subject to subject.

SUMMARY OF THE INVENTION

The invention provides a methodology and system for altering the output of the human vestibular system in a controlled and systematic manner. The invention is based on galvanic vestibular stimulation. With galvanic vestibular stimulation, galvanic current is delivered transcutaneously to the vestibular afferents that lie directly below the mastoid bones. This serves to modulate the continuous firing level of the peripheral vestibular afferents, and causes a standing subject to lean in different directions depending on the polarity of the current and the direction of the subject's head.

The invention utilizes time-varying galvanic vestibular stimulation as the basis for an artificial vestibular control system to reduce or eliminate certain types of pathological postural sway. Such a system can include sensors, e.g., lightweight accelerometers, for monitoring an individual's postural sway, and a galvanic-stimulation control system. In such an arrangement, the sensor output would be used as input to the galvanic-stimulation control system.

A methodology and system of this sort can be used to improve balance control in elderly individuals, who are often predisposed to falls. In addition, patients with vestibular paresis, who have lost some of their hair cells and therefore have a decreased response from the vestibular system during head movement, could also benefit from such a methodology and system. The hair cells, which are responsible for indicating head tilt and acceleration, transmit their information to the vestibular nuclei via the $8^{th}$ nerve. Galvanic vestibular stimulation acts directly on the $8^{th}$ nerve and thus the stimulation technique can be implemented as a vestibular prosthesis to operate in place of the lost hair cells. The invention also utilizes galvanic vestibular stimulation to eliminate or enhance the function of the vestibular system. The former application of the invention can be of use to astronauts, pilots, and sailors. The latter application of the invention can be of use to individuals requiring heightened balance function.

With galvanic vestibular stimulation, small-amplitude galvanic current is delivered transcutaneously to the vestibular afferents that lie directly below the mastoid bones. This serves to modulate the continuous firing level of the peripheral vestibular afferents. Specifically, cathodal (negative) currents increase the firing rate of vestibular afferents, whereas anodal (positive) currents decrease the firing rate of vestibular afferents. Thus, constant bipolar galvanic current produces a tonic vestibular asymmetry. This effect causes a standing subject to lean in different directions depending on the polarity of the current and the direction of the subject's head. In general, a subject will tend to lean toward the anodal stimulus (in the direction of the vestibular apparatus with reduced afferent activity levels), and/or away from the cathodal stimulus (away from the vestibular apparatus with increased afferent activity levels).

With the invention, time-varying binaural galvanic vestibular stimulation is used to produce coherent time-varying postural sway. The galvanic stimulation can be monopolar or bipolar. This application of the invention is based on the aforementioned motor control effects of galvanic vestibular stimulation. With the invention, time-varying galvanic vestibular stimulation is used as the basis for an artificial vestibular control system to reduce or eliminate certain types of pathological postural sway. Such a system would consist of sensors, e.g., lightweight accelerometers, for monitoring an individual's postural sway, and a galvanic-stimulation control system. In such an arrangement, the sensor output would be used as input to the galvanic-stimulation control system.

In addition, with the invention, time-varying monopolar (anodal) binaural galvanic vestibular stimulation is used to eliminate or reduce the function of the vestibular system.

This application of the invention is based on the finding that anodal (positive) currents decrease the firing rate of vestibular afferents. Similarly, with the invention, time-varying monopolar (cathodal) binaural galvanic vestibular stimulation is used to heighten or enhance the function of the vestibular system. This application of the invention is based on the finding that cathodal (negative) currents increase the firing rate of vestibular afferents.

For each of these applications, at least two surface electrodes are placed on the mastoid bones of each subject, one behind each ear, in order to apply the galvanic vestibular stimulation. The appropriate stimulation signals are generated on a microprocessor, e.g., a computer chip, and transmitted to the electrodes via a D/A system and isolation unit.

One advantage of the invention is that it utilizes and exploits the features of existing sensory neurons via non-invasive means. In particular, it uses galvanic stimulation signals to alter the firing behavior of peripheral vestibular afferents. In this manner, the invention can modify the dynamics of the human postural control system.

The invention as described includes the utilization of galvanic vestibular stimulation. A possible future modification of this methodology would be to utilize other forms of stimulation, such as mechanical vibration, to alter the output of the human vestibular system.

The invention provides a non-invasive means for altering the output of the human vestibular system in a controlled and systematic manner. Accordingly, the invention can be used to alter an individual's postural sway in a controlled and systematic manner.

DETAILED DESCRIPTION OF THE INVENTION

Galvanic vestibular stimulation serves to modulate the continuous firing level of the peripheral vestibular afferents. It has been shown that the application of sinusoidally varying bipolar galvanic currents to the vestibular system can lead to sinusoidally varying postural sway. The invention results from testing the hypothesis that stochastic galvanic vestibular stimulation can lead to coherent stochastic postural sway.

In accordance with the invention, nine healthy young subjects (6 females and 3 males, aged 18–30 years; height: 1.63–1.91 m, mean 1.71 m; body weight: 43.1–86.2 kg, mean 62.8 kg) were included in a study. The subjects had no evidence or history of a neurological, gait, postural, or skeletal disorder.

Figure 1:
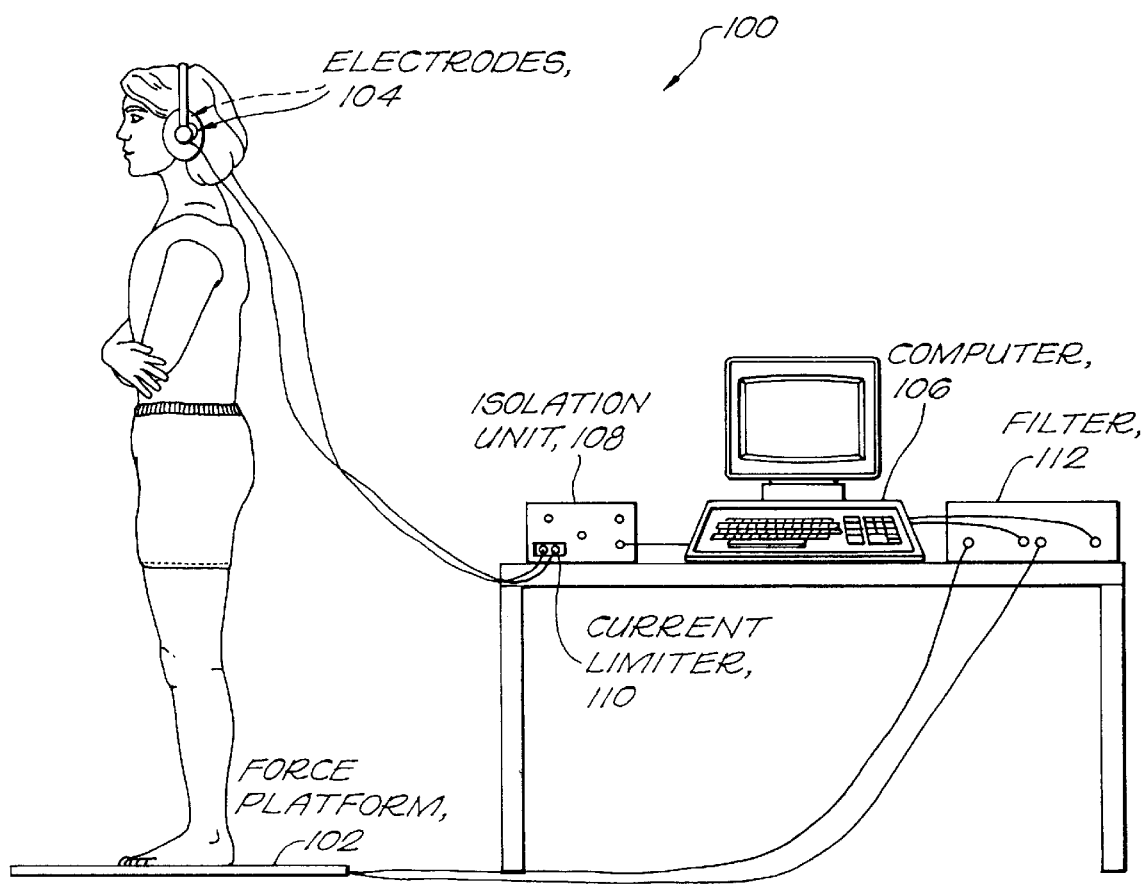
FIG. 1 is a schematic diagram of an exemplary embodiment of a galvanic vestibular stimulation system in accordance with the invention.

FIG. 1 is a schematic diagram of an exemplary embodiment of a galvanic vestibular stimulation system 100 in accordance with the invention. Postural sway was evaluated by using a Kistler 9287 multicomponent force platform 102 to measure the displacements of the COP under a subject's feet. Each subject was instructed to stand upright on the platform in a standardized stance. The subject's feet were separated mediolaterally by a distance of 1–2 cm. During the testing, the subjects stood barefoot with their arms crossed in front and their head facing forward. Subjects were required to close their eyes and wear headphones to block out visual and auditory cues, respectively. Subjects were instructed to relax during the tests and to allow their body to react to the vestibular stimulus.

Two flexible, carbon-rubber, surface electrodes 104 were placed on the mastoid bones of each subject, one behind each ear, in order to apply the galvanic vestibular stimulation. A conductive adhesive gel was used to ensure proper conduction between the skin and the electrodes and to keep the electrodes in place. The electrodes were approximately 9 $cm^2$ in area and kidney-shaped to fit comfortably behind the ears. Stochastic current stimuli were applied binaurally and bipolarly to each subject. The anodal electrode was positioned behind the right ear of each subject, and the cathodal electrode was positioned behind the left ear.

The stochastic stimulus was formed digitally on a computer 106. The stimulus was transmitted via a D/A board to an isolation unit 108 (BAK Electronics, Model BSI-1), which was connected to the electrodes via a current-limiting device 110. The feedback from the platform was fed to the computer via a filter 112.

The stimulus amplitude for individual subjects was determined using the following protocol. Each subject was galvanically stimulated using a sine wave (1–2 Hz) and the amplitude of the stimulus was gradually increased until: (1) the subject felt a mild but not uncomfortable tingling on their skin under the stimulating electrodes, (2) the subject reported a mild sensation of disorientation, and (3) periodic sway at the input frequency was observable. The subject's stimulation level (range 0.4 mA to 1.5 mA, peak-to-peak) was then used as the maximum amplitude limit during the stimulation trials for that subject.

The stimulus x(t) used for galvanic vestibular stimulation was a realization of a stochastic process, given by the first-order autoregressive difference equation $$x(t)=\alpha x(t-1)+\epsilon(t), \ \epsilon(t)\sim N(0,\sigma^2). \tag{1}$$

From a physical standpoint, this process describes a relaxator that is driven by white noise $\epsilon(t)$, with variance $\sigma^2$. The relaxation time $\tau$ of the process can be written in terms of the parameter $\alpha$ as $\tau=-1/\log(|\alpha|)$. In the exemplary study, $\tau=100$ was used.

The spectrum of this process is continuous (it contains all frequencies) and its power is distributed such that it is inversely related to frequency. The second-order spectral properties of this process are thus similar to those of quiet-standing COP data, the power spectra of which decrease with increasing frequencies. This process is, therefore, a more natural choice for a stochastic posture stimulus than a white noise signal, whose power is distributed equally over all frequencies.

The autoregressive process was filtered, using a simple Fourier filter, to create three stimulation signals, each with a different frequency content: 0–1 Hz, 1–2 Hz, and 0–2 Hz. Each of the signals contained a part of the continuous spectrum, e.g., the 0–1 Hz stimulus contained the entire frequency band from 0–1 Hz, with the shape of the aforementioned autoregressive process. Each of the three stimulation signals (duration: 60 sec) was used in five different trials. Each trial was 60 sec in duration and subjects were galvanically stimulated throughout each trial. In addition to the stimulation trials, five 60 sec quiet-standing trials, without galvanic stimulation, were conducted on each subject. Thus, in total, 20 trials were conducted on each subject; 15 stimulation trials and five control (no stimulation) trials. The presentation order of the stimulation and control trials was randomized. The displacements of the COP during each trial were measured with the force platform. To prevent anti-aliasing effects, the COP data were low-pass filtered with filter 112 at 30 Hz during data acquisition. All data were sampled at 100 Hz and stored on the computer for off-line analysis.

The cross-spectrum $CS(\omega)$, where $\omega$ is frequency, of two stationary, zero-mean time series $x(t)$ and $y(t)$ is defined as the Fourier transform (FT) of the cross-correlation function $CCF(t')=<x(t)y(t-t')>$, where $<\cdot>$ denotes expectation. The coherency spectrum $Coh(\omega)$ is defined as the modulus of the normalized cross-spectrum $CS(\omega)$ $$Coh(\omega) = \frac{|CS(\omega)|}{\sqrt{S_x(\omega)S_y(\omega)}} \quad (2)$$

where $S_x(\omega)$ and $S_y(\omega)$ denote the power spectra of $x(t)$ and $y(t)$, respectively, the FT of the respective autocorrelations. The coherency can be interpreted as a measure of linear predictability; it equals one whenever $x(t)$ is a linear function of $y(t)$.

The estimation of the power and cross spectra is achieved by a direct spectral estimation, based on the discrete FT of the recorded data. The periodogram, which is the squared modulus of the discrete FT, is smoothed by a window function $W_j$ to obtain a consistent estimator of the spectra. The simplest form of such a procedure is a sliding average. A triangular window was chosen (the so-called Bartlett estimator) to calculate the spectra because its statistical properties are superior to those of a sliding average. The coherency is then estimated by replacing the spectra in Eq. 2 with their respective estimated quantities.

For each trial, the coherency between the stochastic vestibular stimulation signal $x(t)$ and the resulting COP time series (mediolateral and anteroposterior, respectively) was investigated. It is possible, however, that estimation bias due to misalignment results in an underestimation of coherency. To control for this effect, all time series, i.e., $x(t)$ and the resulting COP time series, were realigned using an iterative procedure. In short, all calculations were performed using $x(t-d)$ instead of $x(t)$, since it is expected that the COP time series lags $x(t)$ by a certain delay $d$. The delay $d$ was estimated using the phase spectra $\Phi(\omega)$ defined by the relationship $$CS(\omega)=|CS(\omega)| \exp(i\Phi(\omega)). \quad (3)$$

Figure 2:
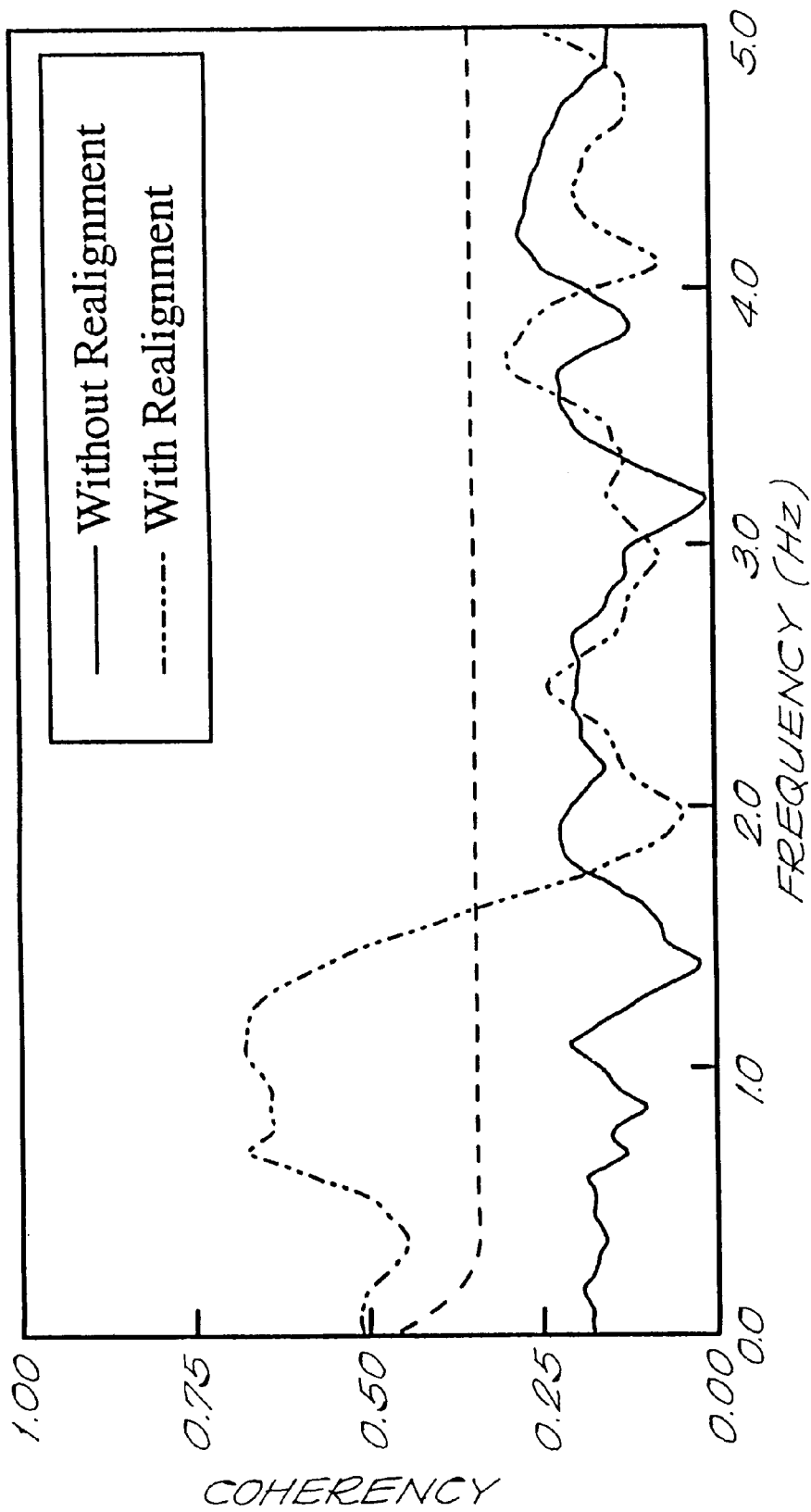
FIG. 2 is a graph providing plots of the coherency between the 0–2 Hz stochastic vestibular stimulation signal and the resulting mediolateral COP time series for a single 60 s trial from one subject.

FIG. 2 is a graph providing plots of the coherency between the 0–2 Hz stochastic vestibular stimulation signal and the resulting mediolateral COP time series for a single 60 sec trial from one subject. The results are shown for the two time series without and with realignment. The dashed line indicates the level of significance, s, for $\alpha=0.95$. It can be seen that realignment resulted in a significant increase in the amount of coherency found between the two time series.

To test each output trial for linear independence from the input stimulus, the power spectra and cross-spectra were estimated by using a direct spectral estimator. The critical value s for the null hypothesis of zero coherency for a given significance level $\alpha$ is $$s = \sqrt{1 - \alpha^{\frac{2}{v-2}}}, \quad (4)$$

where $v$ is the so-called equivalent number of degrees of freedom, which depends on the direct spectral estimator, i.e., on $W_j$ and the tapering used.

To determine whether two series are uncorrelated, it is not sufficient to consider simply the value s. The reason is that the derivation of the underlying statistics that lead to a test based on Eq. 4 assumes that the cross spectrum is approximately constant over the width of the window function $W_j$ used in the direct spectral estimation. Asymptotically, this assumption is always true given the required properties of a valid smoothing window function $W_j$. If, however, a cross spectrum of a finite series exhibits a high curvature, then the confidence interval is no longer valid. To overcome this problem, investigators commonly use a technique known as "prewhitening", in which one (or two) of the series is linearly filtered so that the cross spectrum of the resulting, filtered series is flat. This can be done because a linear filter applied to one or both of the signals does not modify the coherency. In the exemplary studies, the stochastic vestibular stimulation signal was prewhitened before the coherency was calculated. Since the parameter $\alpha$ was known in Eq. 1, $x(t)$ is able to be prewhitened simply by inverting the filter of Eq. 1.

In addition to the above tests, an average coherency between the respective vestibular stimulation signals and the significantly dependent COP time series was also determined for each subject. The average was taken for all values within the broadest contiguous frequency band of significant coherency. If the contiguous frequency band showing significant coherency was smaller than 0.5 Hz (which was the width of the spectral estimator $W_j$), then the bandwidth of the stochastic stimulation signal (0–1 Hz, 1–2 Hz, or 0–2 Hz) was taken by default.

Figure 3A:
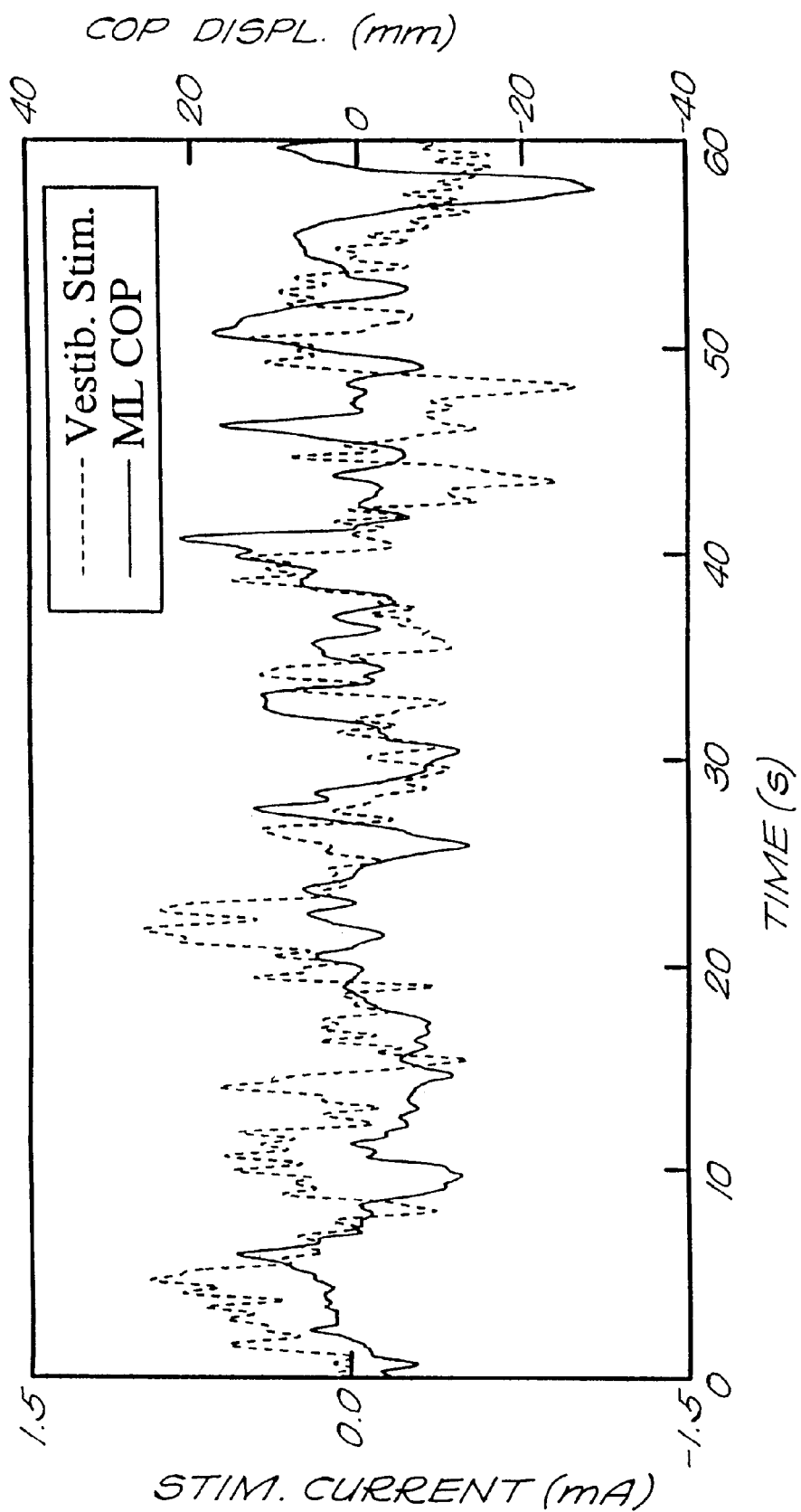
FIG. 3A is a graph showing a plot of the 0–2 Hz stochastic vestibular stimulation signal and the resulting mediolateral COP time series for a single 60 s trial from one subject.
Figure 3B:
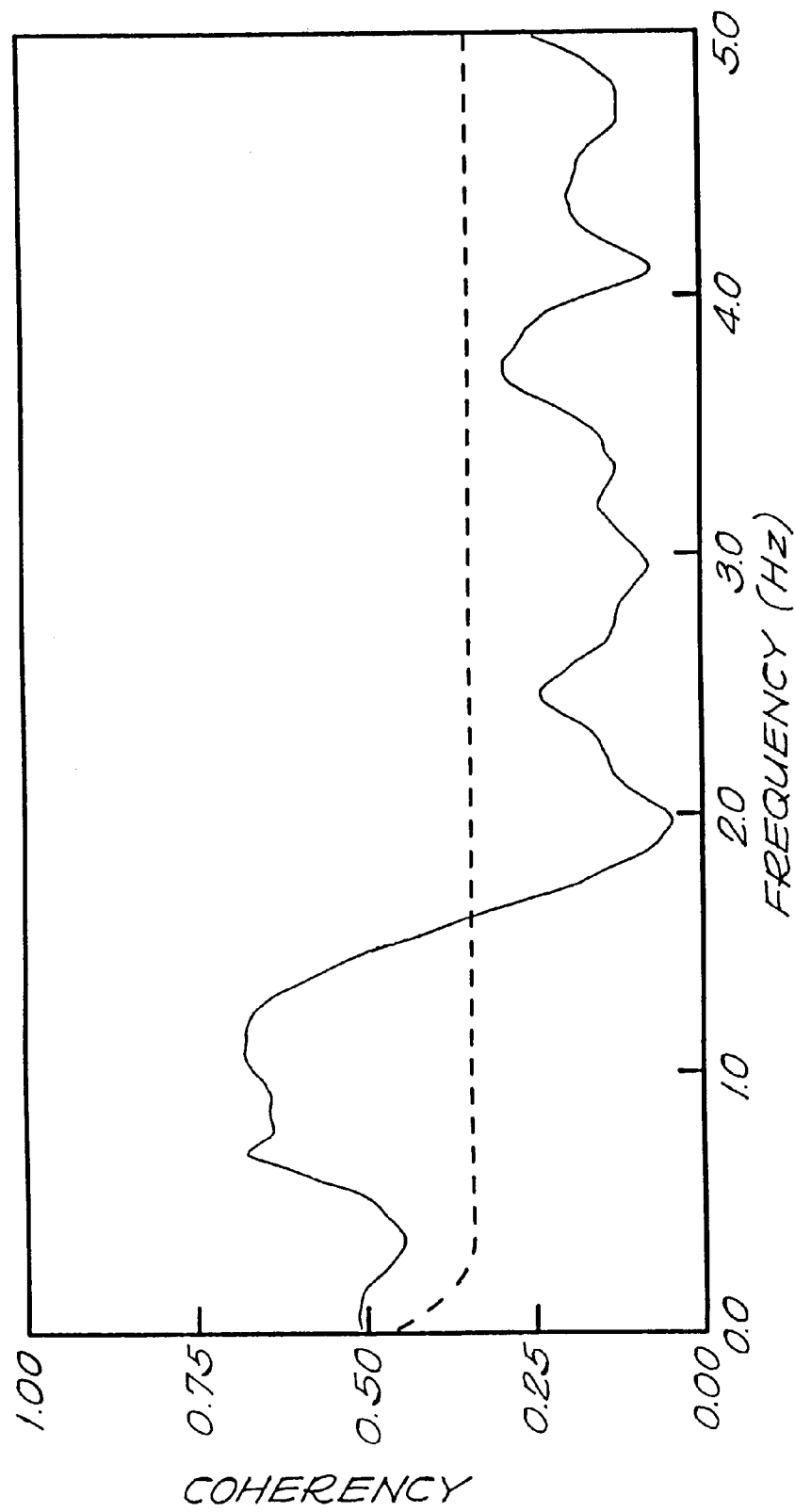
FIG. 3B is a graph showing a plot of the coherency between the vestibular stimulation signal and the COP time series in FIG. 3A.

The 0–2 Hz stochastic vestibular stimulus and the resulting mediolateral COP time series for a single 60 s trial from one subject are shown in the graph of FIG. 3A. The figure demonstrates the difficulty in determining by visual inspection whether there is a relationship between the two time series. The coherency plot for the two series in FIG. 3A is shown in the graph of FIG. 3B. The dashed line indicates the level of significance, s, for $\alpha=0.95$ (see Eq. 4). It can be seen that there is significant coherency between the vestibular stimulus and the mediolateral COP time series at frequencies less than 2.0 Hz, i.e., at frequencies less than the upper limit of the filtered input stimulus.

Figure 4A:
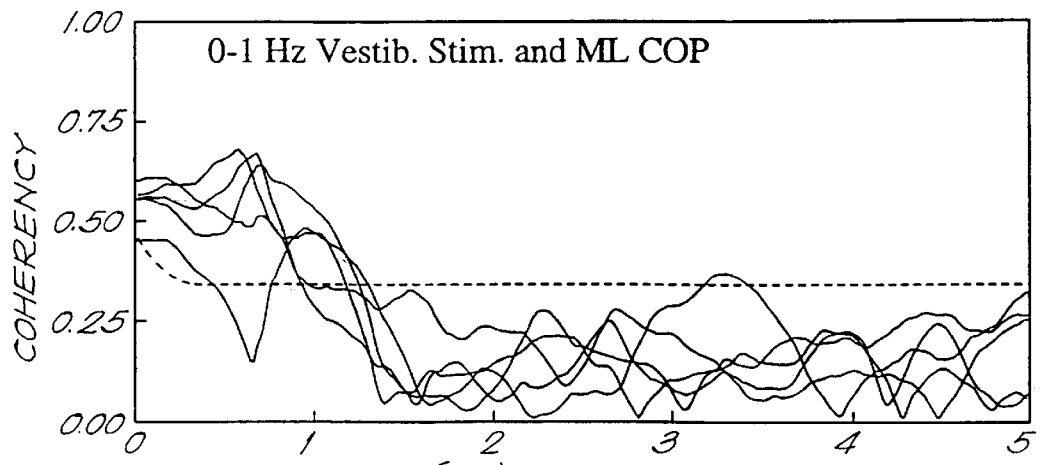
FIGS. 4A–4C are graphs showing plots of the coherency between the stochastic vestibular stimulation signal and the resulting mediolateral COP time series for each trial from the subject of FIGS. 3A and 3B.
Figure 4B:
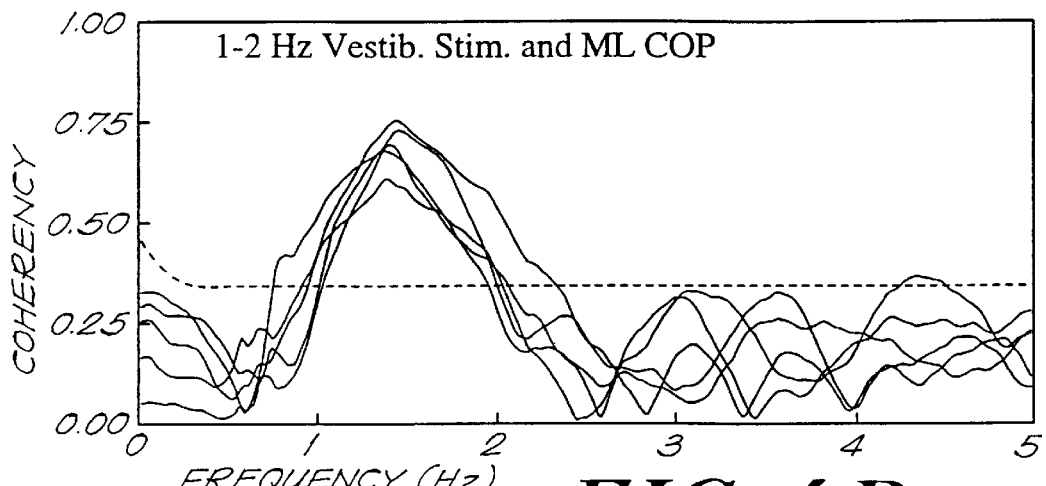
Figure 4C:
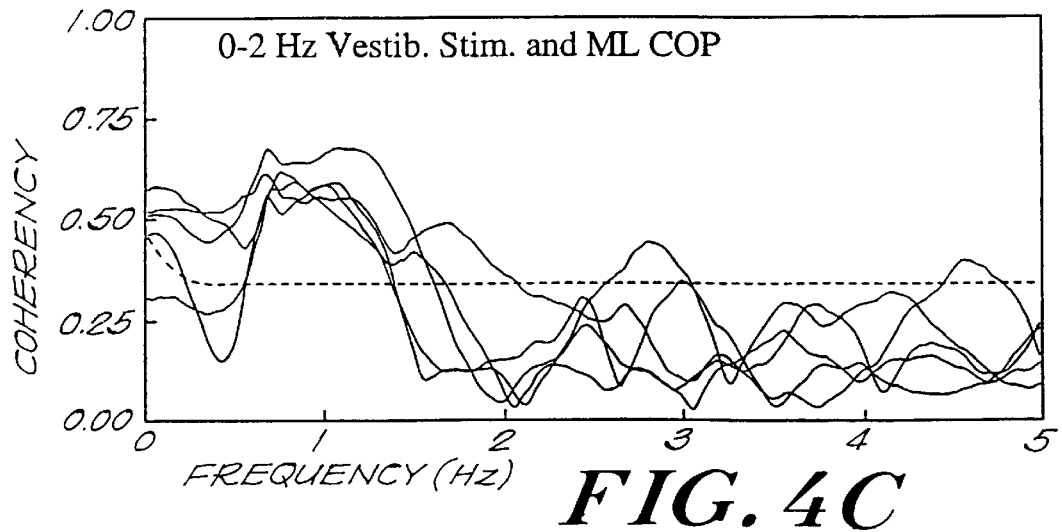

FIGS. 4A–4C provide the coherency results for the three different stochastic vestibular stimulation signals, i.e., signals that were bandlimited between 0–1 Hz (FIG. 4A), 1–2 Hz (FIG. 4B), and 0–2 Hz (FIG. 4C), for the subject in FIGS. 3A–3B. It can be seen that for each single trial, there is significant coherency between the vestibular stimulus and the mediolateral COP time series at frequencies less than the upper limit of the filtered input stimulus. In addition, it can be seen that the coherency results for each stimulation signal were highly reproducible from trial to trial (FIGS. 4A–4C), i.e., the coherency plots for the five trials for a given stimulus have similar shapes. The dashed line indicates the level of significance, s, for $\alpha=0.95$ (see Eq. 4).

As expected, the position of the maximum coherency varied with the frequency band of the different stimulation signals and was observed within the respective frequency band. These general results were found in eight of the nine subjects tested. In particular, significant coherency between the stochastic vestibular stimulation signal and the resulting mediolateral COP time series was found in 12–15 trials (out of a possible 15) for each of these subjects. The ninth subject only exhibited significant coherency in six trials; this reduced level of coherency might have occurred because the subject did not appear to relax during the testing, as instructed.

Figure 5A:
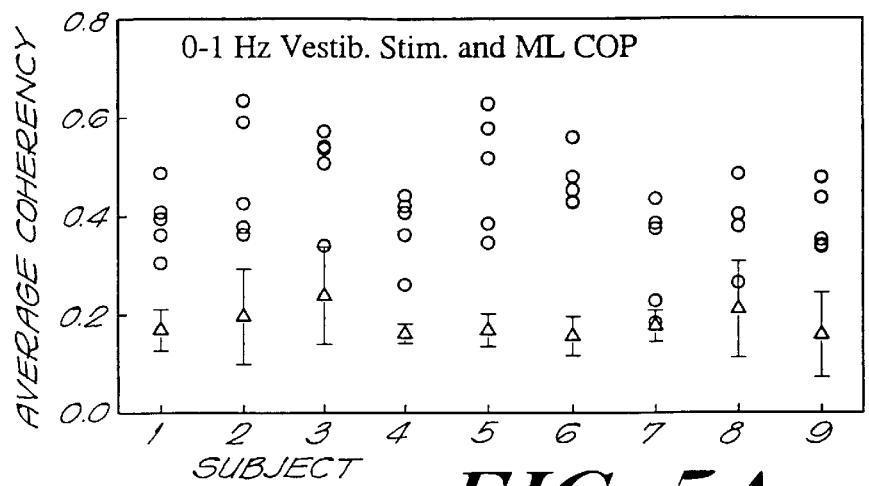
FIGS. 5A–5C are graphs showing the average coherency values between the respective vestibular stimulation signals and the resulting mediolateral COP time series for the significant coherent trials.
Figure 5B:
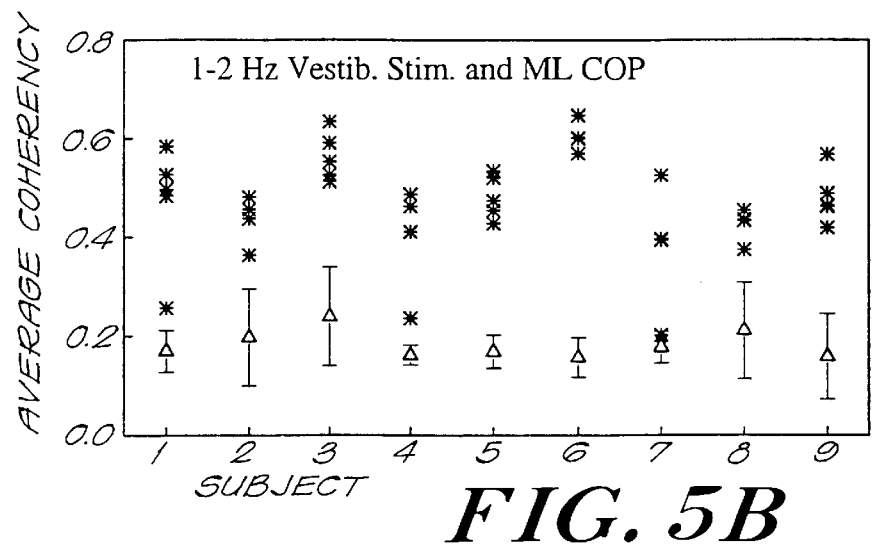
Figure 5C:
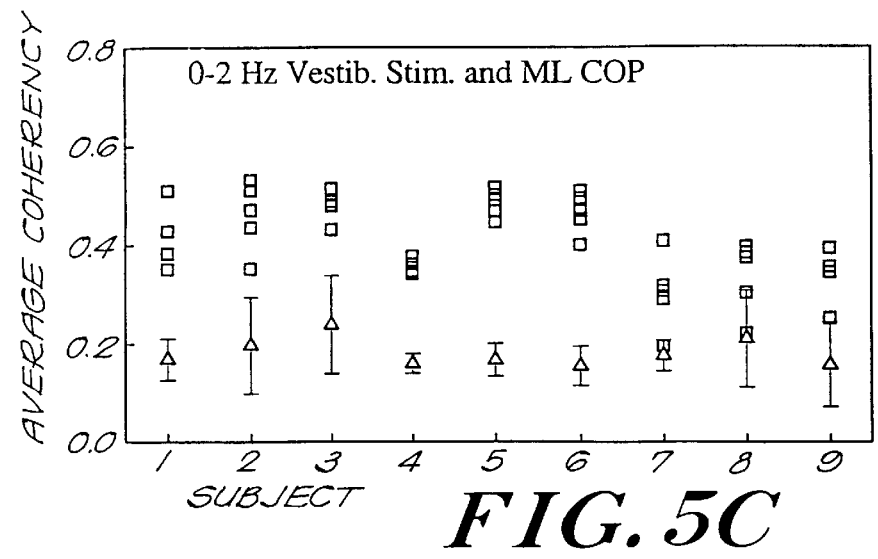

FIG. 5 is a graph showing the average coherency values between the respective vestibular stimulation signals and the resulting mediolateral COP time series for the significant coherent trials from each of the nine subjects. Shown are the results for the (a) 0–1 Hz (FIG. 5A), (b) 1–2 Hz (FIG. 5B), and (c) 0–2 Hz (FIG. 5C) vestibular stimulation signals. The number of points plotted for each subject corresponds to the number of significant coherent trials for that subject. Note that the values plotted in FIGS. 5A–5C are slightly lower than the peak values, e.g., see FIGS. 4A–4C, since they correspond to an average over a frequency band. It should also be noted that for each subject the average coherency for a given stimulation signal was consistent from trial to trial. Moreover, in general, the highest degree of coherency was found for the 1–2 Hz stochastic vestibular stimulation signal.

Figure 6A:
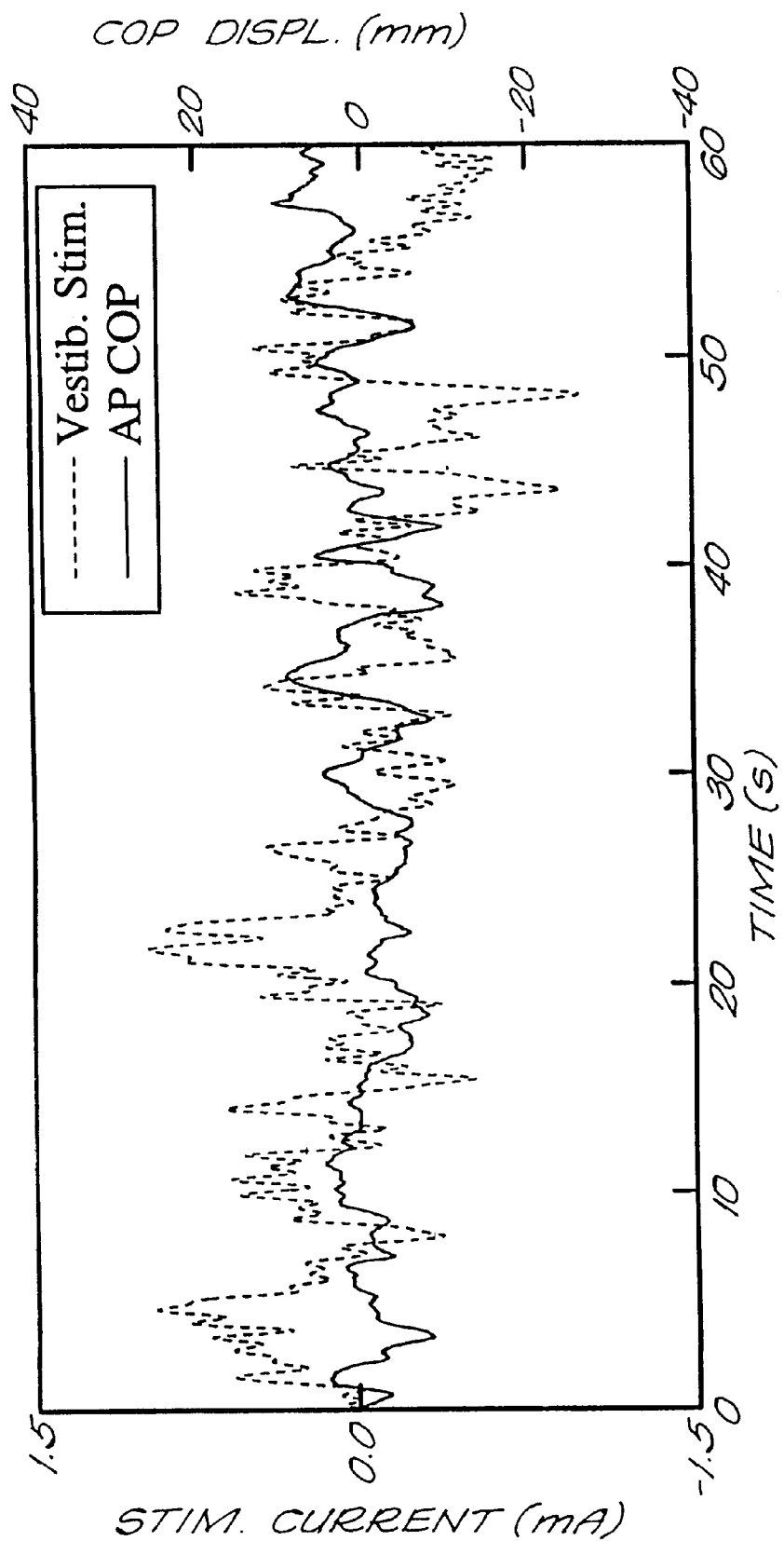
FIG. 6A is a graph showing a plot of the 0–2 Hz stochastic vestibular stimulation signal and the resulting anteroposterior COP time series for a single 60 s trial from one subject.
Figure 6B:
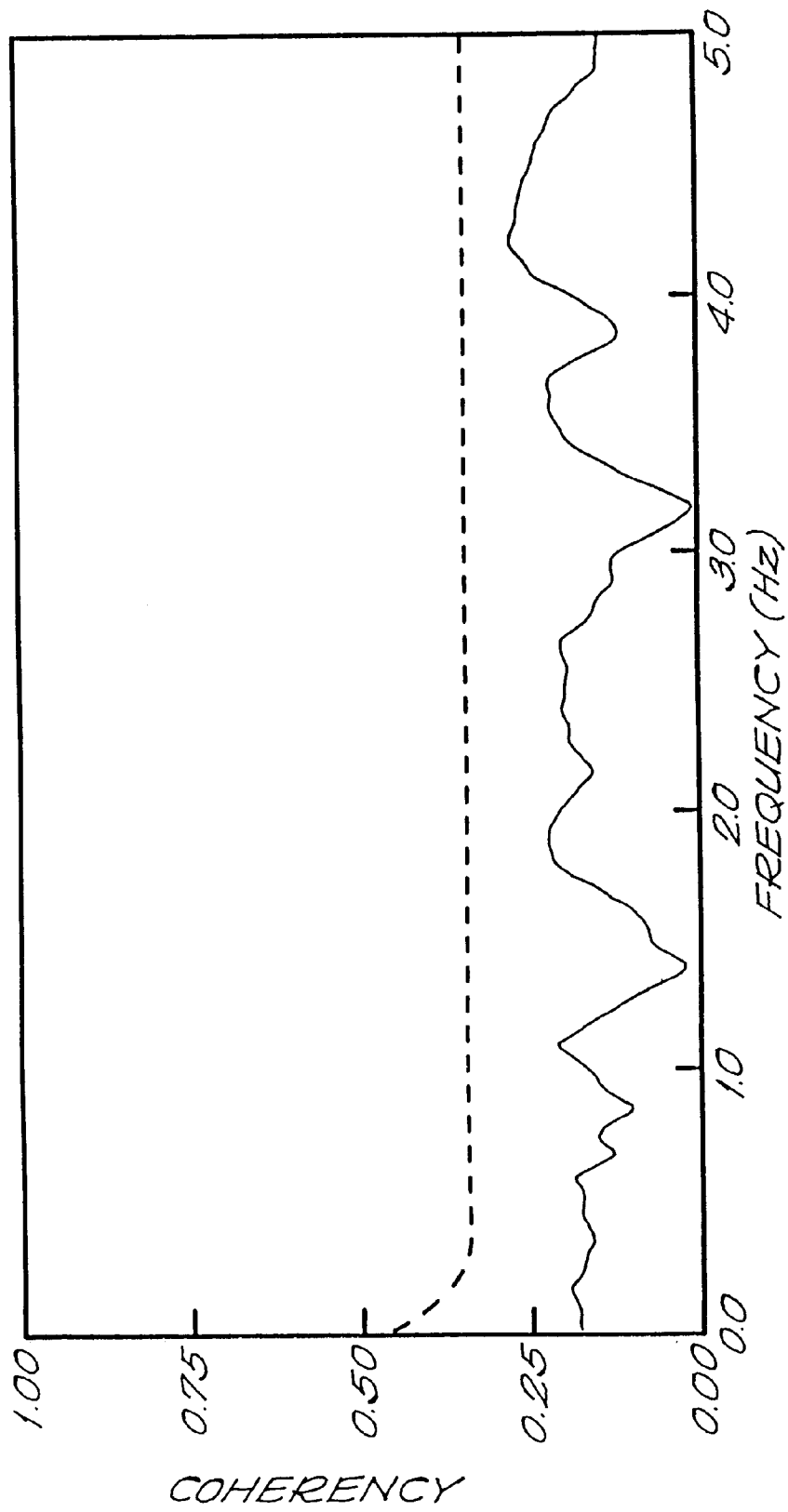
FIG. 6B is a graph showing a plot of the coherency between the vestibular stimulation signal and the COP time series in FIG. 6A.

The 0–2 Hz stochastic vestibular stimulus and the resulting anteroposterior COP time series for a single 60 s trial from one subject are shown in the graph of FIG. 6A. The corresponding coherency plot for that trial is shown in the graph of FIG. 6B. The dashed line indicates the level of significance, s, for $\alpha=0.95$ (see Eq. 4). It can be seen that there is no significant coherency between the vestibular stimulus and the anteroposterior COP time series.

Figure 7A:
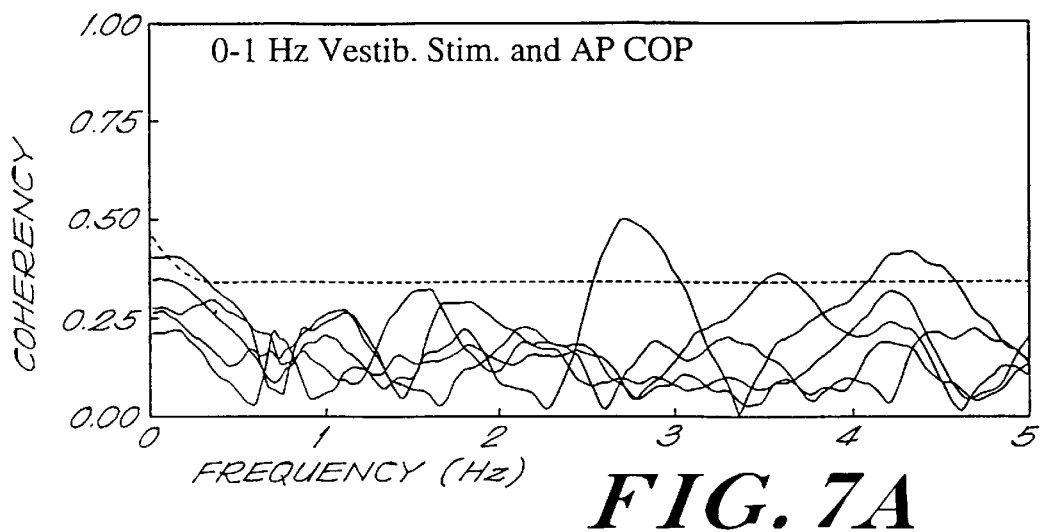
FIGS. 7A–7C are graphs with plots of the coherency between the stochastic vestibular stimulation signal and the resulting anteroposterior COP time series for each trial from the subject of FIGS. 3A and 3B.
Figure 7B:
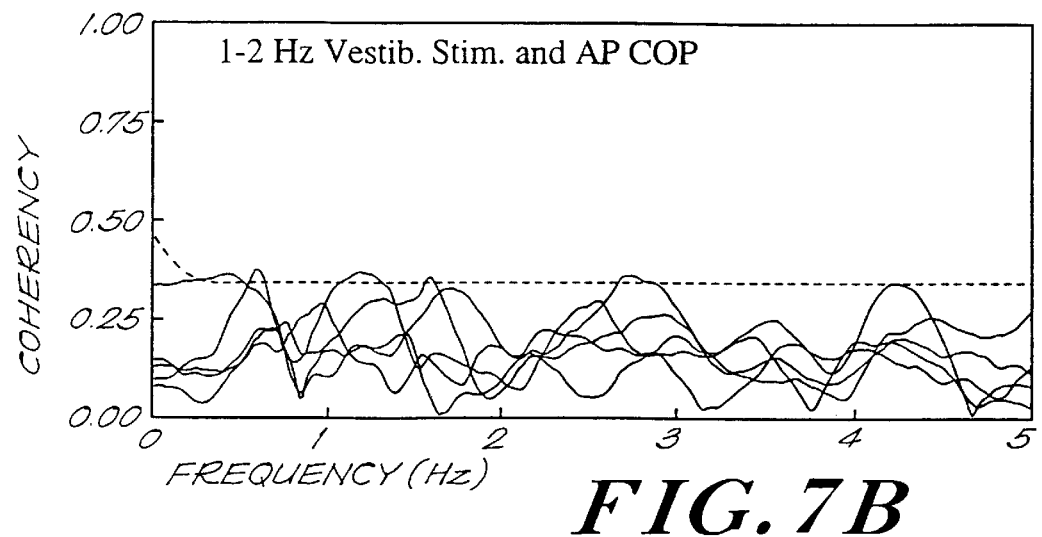
Figure 7C:
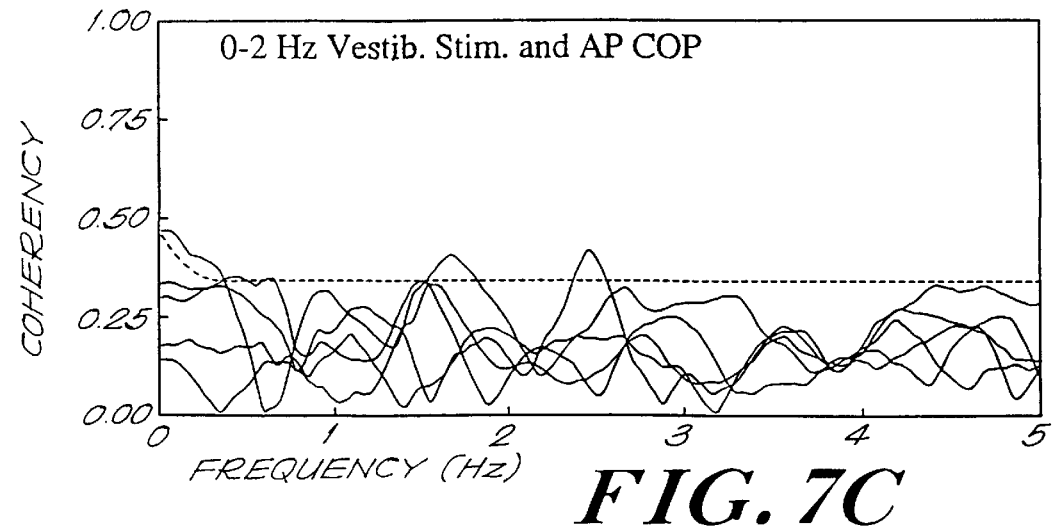

Similar results were obtained for all subjects. FIGS. 7A–7C are graphs with plots of the coherency between the stochastic vestibular stimulation signal and the resulting anteroposterior COP time series for each trial from the subject of FIGS. 3A–3B. The graphs show the results for the (a) 0–1 Hz (FIG. 7A), (b) 1–2 Hz (FIG. 7B), and 0–2 Hz (FIG. 7C) vestibular stimulation signals. Five trials were conducted for each stimulation signal. The dashed line indicates the level of significance, s, for $\alpha=0.95$ (see Eq. 4).

Figure 8A:
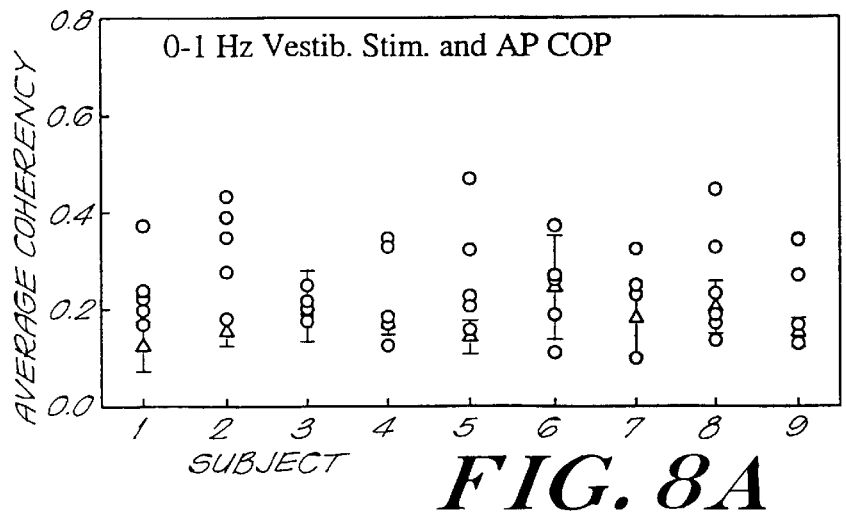
FIGS. 8A–8C are graphs showing the average coherency values between the respective vestibular stimulation signals and the resulting anteroposterior COP time series for the different trials from each of the nine subjects.
Figure 8B:
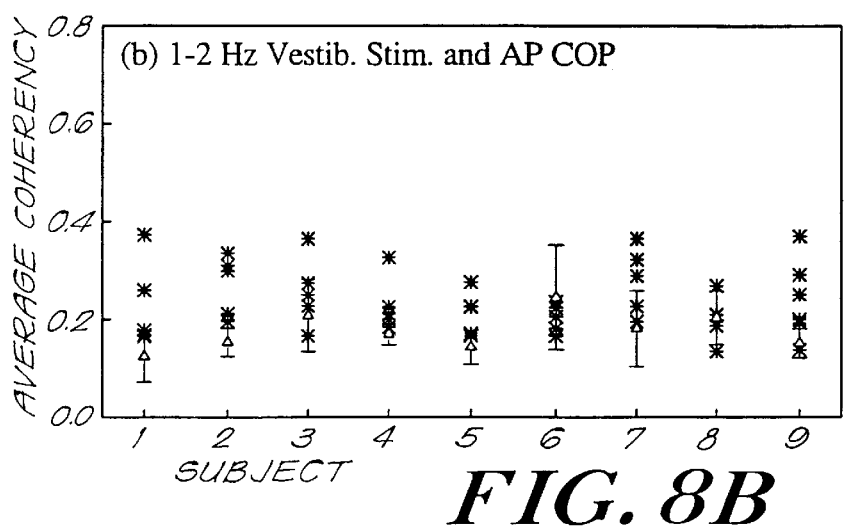
Figure 8C:
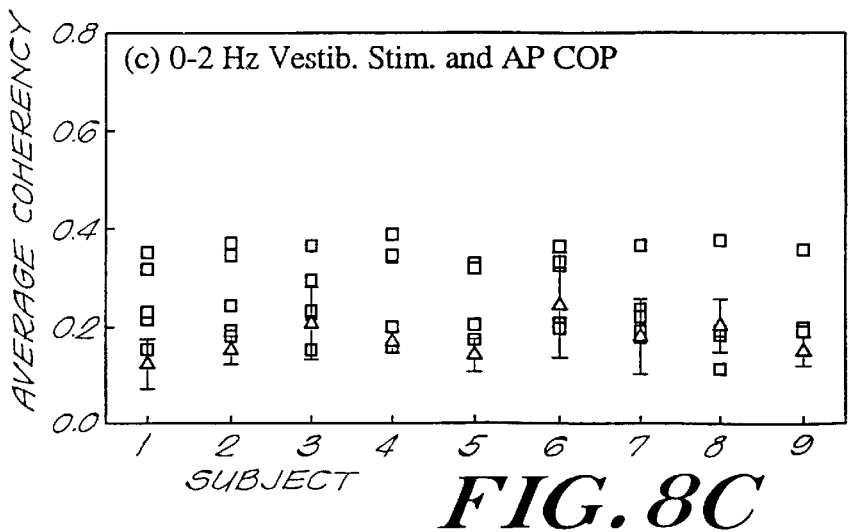

FIGS. 8A–8C are graphs showing the average coherency values between the respective vestibular stimulation signals and the resulting anteroposterior COP time series for the different trials from each of the nine subjects. The graphs show the results for the (a) 0–1 Hz (FIG. 8A), (b) 1–2 Hz (FIG. 8B), and 0–2 Hz (FIG. 8C) vestibular stimulation signals. The mean values and standard deviations of the average coherency for the control (no stimulation) trials are also given in each plot.

In accordance with the invention, it has been demonstrated that in subjects who are facing forward, bipolar binaural stochastic galvanic stimulation of the vestibular system leads to coherent stochastic mediolateral postural sway. Specifically, significant coherency between the stochastic vestibular stimulation signal and the resulting mediolateral COP time series has been found in the majority of trials in 8 of the 9 subjects tested. The coherency values obtained were up to 0.8 for several trials.

It was also found that in subjects who are facing forward, bipolar binaural stochastic galvanic stimulation of the vestibular system does not lead to coherent stochastic anteroposterior postural sway. This result is consistent with the conventional findings that show that with bipolar binaural constant galvanic vestibular stimulation, the direction of the evoked sway is approximately in the direction of the intermastoid line. Thus, it is possible that coherent stochastic anteroposterior sway could be produced with bipolar binaural stochastic galvanic vestibular stimulation if the subject's head is turned to the left or right (over the left or right shoulder).

Other conventional studies have shown that if a subject's head is facing forward, monopolar binaural constant galvanic stimulation of the vestibular system can be used to induce anteroposterior sway in the subject. Thus, it is also possible that coherent stochastic anteroposterior postural sway could be produced with monopolar binaural stochastic galvanic vestibular stimulation.

Previous studies have suggested that the role of the vestibular system is to modulate the amplitude of the body's postural response. The results of the study in accordance with the invention support this notion. In particular, it has been shown that time-varying galvanic vestibular stimulation can continuously modulate mediolateral postural sway. In addition, by utilizing stochastic stimulation signals, the subjects could not predict a change in the vestibular stimulus. Thus, the findings indicate that subjects can act as "responders" to galvanic vestibular stimulation.

The findings in accordance with the invention indicate that time-varying galvanic vestibular stimulation could be used as the basis for an artificial vestibular control system to reduce or eliminate certain types of pathological postural sway. Such a system could consist of light-weight accelerometers for monitoring an individual's postural sway, and a galvanic-stimulation control system. In such an arrangement, the accelerometer output could be used as input to the galvanic-stimulation control system.

A system of this sort could be used to improve balance control in elderly individuals, who are often predisposed to falls. In addition, patients with vestibular paresis, who have lost some of their hair cells and therefore have a decreased response from the vestibular system during head movement, could also benefit from such a system. The hair cells, which are responsible for indicating head tilt and acceleration, transmit their information to the vestibular nuclei via the $8^{th}$ nerve. Galvanic vestibular stimulation acts directly on the $8^{th}$ nerve and the stimulation technique of the invention could be implemented as a vestibular prosthesis to operate in place of the lost hair cells.

In addition, in accordance with the invention, time-varying monopolar (anodal) binaural galvanic vestibular stimulation is used to eliminate or reduce the function of the vestibular system. This application of the invention is based on the finding that anodal (positive) currents decrease the firing rate of vestibular afferents. Similarly, with the invention, time-varying monopolar (cathodal) binaural galvanic vestibular stimulation is used to heighten or enhance the function of the vestibular system. This application of the invention is based on the finding that cathodal (negative) currents increase the firing rate of vestibular afferents.

Although the present invention has been shown and described with respect to several preferred embodiments thereof, various changes, omissions and additions to the form and detail thereof, may be made therein, without departing from the spirit and scope of the invention.

What is claimed is:

1. A method of altering the output of a vestibular system comprising:

providing a source of time-varying galvanic current;

transcutaneously delivering time-varying galvanic current to vestibular afferents associated with said vestibular system in order to modulate firing level of said vestibular afferents; and inducing a coherent time-varying sway response that counteracts postural sway.

2. The method of claim 1, wherein said firing level is increased in response to delivering cathodal galvanic currents.

3. The method of claim 1, wherein said firing level is decreased in response to delivering anodal galvanic currents.

4. The method of claim 1, wherein said postural sway is self-generated.

5. The method of claim 1, wherein said postural sway is externally-generated.

6. The method of claim 1 further comprising monitoring postural sway in order to determine the characteristics of the galvanic current to be delivered.

7. The method of claim 1, wherein said coherent time-varying sway reduces said postural sway.

8. The method of claim 1, wherein said coherent time-varying sway eliminates said postural sway.

9. A galvanic vestibular stimulation system comprising:

a source of time-varying galvanic current; and a delivery module which transcutaneously delivers time-varying galvanic current to vestibular afferents associated with said vestibular system in order to modulate firing level of said vestibular afferents; and means for inducing a coherent time-varying sway response that counteracts postural sway.

10. The system of claim 9, wherein said firing level is increased in response to delivering cathodal galvanic currents.

11. The system of claim 9, wherein said firing level is decreased in response to delivering anodal galvanic currents.

12. The system of claim 9, wherein said postural sway is self-generated.

13. The system of claim 9, wherein said postural sway is externally-generated.

14. The system of claim 9 further comprising a monitor that monitors postural sway in order to determine the characteristics of the galvanic current to be delivered.

15. The system of claim 9, wherein said coherent time-varying sway reduces said postural sway.

16. The system of claim 9, wherein said coherent time-varying sway eliminates said postural sway.

17. A galvanic vestibular stimulation system comprising:

a time-varying galvanic current source which transcutaneously delivers time-varying galvanic current to vestibular afferents in order to modulate the firing level of said vestibular afferents;

a monitor which monitors postural sway thereby providing indication of necessary galvanic current to be delivered; and means for inducing a coherent time-varying sway response that counteracts the monitored postural sway.

* * * * *